US008491509B2

(12) United States Patent
Trandafir

(10) Patent No.: US 8,491,509 B2
(45) Date of Patent: Jul. 23, 2013

(54) APPARATUS AND METHOD FOR MONITORING AND CONTROLLING THE TRANSMISSIBILITY OF MECHANICAL VIBRATION ENERGY DURING DYNAMIC MOTION THERAPY

(76) Inventor: Titi Trandafir, S. Plainfield, NJ (US)

( * ) Notice: Subject to any disclaimer, the term of this patent is extended or adjusted under 35 U.S.C. 154(b) by 0 days.

(21) Appl. No.: 11/388,286

(22) Filed: Mar. 24, 2006

(65) Prior Publication Data

US 2006/0217640 A1 Sep. 28, 2006

Related U.S. Application Data

(60) Provisional application No. 60/665,013, filed on Mar. 24, 2005.

(51) Int. Cl.
*A61H 7/00* (2006.01)
*A61H 19/00* (2006.01)
*A61B 5/103* (2006.01)
*A61B 5/117* (2006.01)

(52) U.S. Cl.
USPC ................................ 601/90; 601/93; 600/595

(58) Field of Classification Search
USPC ................ 601/84, 86, 87, 89, 90, 93, 98, 23, 601/27, 100, 29–32, 34, 35, 101, 104; 600/595, 600/587
See application file for complete search history.

(56) References Cited

U.S. PATENT DOCUMENTS 3,890,953 A 6/1975 Kraus et al.
4,105,017 A 8/1978 Ryaby et al.
4,266,532 A 5/1981 Ryaby et al.
4,266,533 A 5/1981 Ryaby et al.
4,315,503 A 2/1982 Ryaby et al.
4,530,360 A 7/1985 Duarte
4,570,927 A 2/1986 Petrofsky et al.
5,103,806 A 4/1992 McLeod et al.
5,191,880 A 3/1993 McLeod et al.
5,273,028 A 12/1993 McLeod et al.
RE34,663 E * 7/1994 Seale ............................ 128/774
5,376,065 A 12/1994 McLeod et al.
5,484,388 A * 1/1996 Bassett et al. ................... 601/27
5,997,490 A 12/1999 McLeod et al.

(Continued)

FOREIGN PATENT DOCUMENTS

WO WO 02/053084 7/2002

OTHER PUBLICATIONS

PCT Transmittal of International Search Report dated Jul. 20, 2006 for PCT/US2006/010753.

*Primary Examiner* — Justine R Yu
*Assistant Examiner* — Kristen C Matter

(57) ABSTRACT

Apparatus and methods for therapeutically treating bone fractures, osteopenia, osteoporosis, or other tissue conditions, postural instability, or other conditions, such as cystic fibrosis, Crohn's disease and kidney and gall bladder stones. An oscillating platform apparatus supports a body to be treated. An oscillator is positioned within the platform apparatus and is configured to impart an oscillating force on the body. Two accelerometers are mounted to the platform apparatus for determining the acceleration and weight of the body. Once the weight of the body is determined, the amplitude of the frequency of the oscillating force and/or frequency of the oscillating force is adjusted to provide a desired therapeutic treatment to the patient. Information received from the two accelerometers is also used to determine the posture of the patient and the transmissibility of the mechanical vibration energy generated by the oscillating force through the body.

36 Claims, 4 Drawing Sheets

U.S. PATENT DOCUMENTS

| | | | | |
|---|---|---|---|---|
| 6,022,349 | A | 2/2000 | McLeod et al. | |
| 6,063,046 | A * | 5/2000 | Allum | 600/595 |
| 6,234,975 | B1 | 5/2001 | McLeod et al. | |
| 6,607,497 | B2 | 8/2003 | McLeod et al. | |
| 6,620,117 | B1 * | 9/2003 | Johnson et al. | 601/90 |
| 6,843,776 | B2 | 1/2005 | Trandafir et al. | |
| 7,094,211 | B2 * | 8/2006 | Krompasick | 601/90 |
| 2002/0077570 | A1 | 6/2002 | McLeod et al. | |
| 2004/0092848 | A1 | 5/2004 | Trandafir et al. | |
| 2006/0047230 | A1 | 3/2006 | Talish | |

* cited by examiner

APPARATUS AND METHOD FOR MONITORING AND CONTROLLING THE TRANSMISSIBILITY OF MECHANICAL VIBRATION ENERGY DURING DYNAMIC MOTION THERAPY

PRIORITY

The present application claims priority to a U.S. Provisional Application filed on Mar. 24, 2005 and assigned U.S. Provisional Application Ser. No. 60/665,013.

REFERENCE TO RELATED APPLICATIONS

The present application is related to U.S. patent application Ser. No. 10/290,839 filed on Nov. 8, 2002 and U.S. patent application Ser. No. 10/448,942 filed on May 30, 2003 and issued on Jan. 18, 2005 as U.S. Pat. No. 6,843,776 B2; the latter application is a continuation-in-part application of the former application. The entire contents of the patent application and patent are incorporated herein by reference.

BACKGROUND

The present disclosure generally relates to the field of stimulating tissue growth and healing, and more particularly to an apparatus and method for monitoring and controlling the transmissibility of mechanical vibration energy during dynamic motion therapy. More specifically, the present disclosure relates to therapeutically treating damaged tissues, bone fractures, osteopenia, osteoporosis, or other tissue conditions, as well as postural instability, using dynamic motion therapy and mechanical impedance methods to predict and maximize the transmissibility of mechanical vibration energy through a patient's body.

When damaged, tissues in a human body such as connective tissues, ligaments, bones, etc. all require time to heal. Some tissues, such as a bone fracture in a human body, require relatively longer periods of time to heal. Typically, a fractured bone must be set and then the bone can be stabilized within a cast, splint or similar type of device. This type of treatment allows the natural healing process to begin. However, the healing process for a bone fracture in the human body may take several weeks and may vary depending upon the location of the bone fracture, the age of the patient, the overall general health of the patient, and other factors that are patient-dependent. Depending upon the location of the fracture, the area of the bone fracture or even the patient may have to be immobilized to encourage complete healing of the bone fracture. Immobilization of the patient and/or bone fracture may decrease the number of physical activities the patient is able to perform, which may have other adverse health consequences. Osteopenia, which is a loss of bone mass, can arise from a decrease in muscle activity, which may occur as the result of a bone fracture, bed rest, fracture immobilization, joint reconstruction, arthritis, and the like. However, this effect can be slowed, stopped, and even reversed by reproducing some of the effects of muscle use on the bone. This typically involves some application or simulation of the effects of mechanical stress on the bone.

Promoting bone growth is also important in treating bone fractures, and in the successful implantation of medical prostheses, such as those commonly known as "artificial" hips, knees, vertebral discs, and the like, where it is desired to promote bony ingrowth into the surface of the prosthesis to stabilize and secure it. Numerous different techniques have been developed to reduce the loss of bone mass. For example, it has been proposed to treat bone fractures by application of electrical voltage or current signals (e.g., U.S. Pat. Nos. 4,105,017; 4,266,532; 4,266,533, or 4,315,503). It has also been proposed to apply magnetic fields to stimulate healing of bone fractures (e.g., U.S. Pat. No. 3,890,953). Application of ultrasound to promoting tissue growth has also been disclosed (e.g., U.S. Pat. No. 4,530,360).

While many suggested techniques for applying or simulating mechanical loads on bone to promote growth involve the use of low frequency, high magnitude loads to the bone, this has been found to be unnecessary, and possibly also detrimental to bone maintenance. For instance, high impact loading, which is sometimes suggested to achieve a desired high peak strain, can result in fracture, defeating the purpose of the treatment.

It is also known in the art that low level, high frequency stress can be applied to bone, and that this will result in advantageous promotion of bone growth. One technique for achieving this type of stress is disclosed, e.g., in U.S. Pat. Nos. 5,103,806; 5,191,880; 5,273,028; 5,376,065; 5,997,490; and 6,234,975, the entire contents of each of which are incorporated herein by reference. In this technique (referred to as dynamic motion therapy), the patient is supported by an oscillating platform apparatus that can be actuated to oscillate vertically, so that resonant vibrations caused by the oscillation of the platform, together with acceleration brought about by the body weight of the patient, provides stress levels in a frequency range sufficient to prevent or reduce bone loss and enhance new bone formation. The peak-to-peak vertical displacement of the platform oscillation may be as little as 2 μm.

However, these systems and associated methods often depend on an arrangement whereby the operator or user must measure the weight of the patient and make adjustments to the frequency of oscillation to achieve the desired therapeutic effect. U.S. Pat. No. 6,843,776 discloses an oscillating platform apparatus that automatically measures the weight of the patient and adjusts characteristics of the oscillation force as a function of the measured weight, to therapeutically treat damaged tissues, bone fractures, osteopenia, osteoporosis, or other tissue conditions.

It is an aspect of the present disclosure to provide an alternative oscillating platform apparatus and associated circuitry for determining the weight of the patient using two angular measurements and making adjustments to the frequency of oscillation and/or the amplitude of the frequency of oscillation in accordance with the calculated weight of the patient to achieve the desired therapeutic effect.

It is also known in the art that the application of low level, high frequency stress is effective in treating postural instability. A method of using resonant vibrations caused by the oscillation of a vibration table or unstable vibrating platform for treating postural instability is described in U.S. Pat. No. 6,607,497 B2; the entire contents of which are incorporated herein by reference. The method includes the steps of (a) providing a non-invasive dynamic therapy device having a vibration table with a non-rigidly supported platform; (b) permitting the patient to rest on the non-rigidly supported platform for a predetermined period of time; and (c) repeating the steps (a) and (b) over a predetermined treatment duration. Step (b) includes the steps of (b1) measuring a vibrational response of the patient's musculoskeletal system using a vibration measurement device; (b2) performing a frequency decomposition of the vibrational response to quantify the vibrational response into specific vibrational spectra; and (b3) analyzing the vibrational spectra to evaluate at least postural stability.

The method described in U.S. Pat. No. 6,607,497 B2 entails the patient standing on the vibration table or the unstable vibrating platform. The patient is then exposed to a vibrational stimulus by the unstable vibrating platform. The unstable vibrating platform causes a vibrational perturbation of the patient's neuro-sensory control system. The vibrational perturbation causes signals to be generated within at least one of the patient's muscles to create a measurable response from the musculoskeletal system. These steps are repeated over a predetermined treatment duration for approximately ten minutes a day in an effort to improve the postural stability of the patient.

The patient undergoing vibrational treatment for treating postural instability and/or the promotion of bone growth, as described above, may experience a level of discomfort due to whole-body vibration acceleration. The level of discomfort caused by vibration acceleration depends on the vibration frequency, the vibration direction, the point of contact with the body, and the duration of the vibration exposure. It is desirable to monitor at least one mechanical response of the body during vibrational treatment in an effort to control the at least one mechanical response to influence comfort level, as well as to determine patient- and treatment-related characteristics. Two mechanical responses of the body that are often used to describe the manner in which vibration causes the body to move are transmissibility and mechanical impedance.

Transmissibility describes the fractional relationship of the vibration which is transmitted from, say, the vibration table or oscillating platform apparatus to the head of the patient. The transmissibility of the body is highly dependent on vibration frequency, vibration axis and body posture. Vertical vibration on The non-invasive dynamic therapy device causes vibration in several axes at the head; for vertical head motion, the transmissibility tends to be greatest in the approximate range of 3 to 10 Hz.

The mechanical impedance of the body shows the force that is required to make the body move at each frequency. Although the impedance depends on body weight, the vertical impedance of the human body usually shows a resonance at about 5 Hz. The mechanical impedance of the body, including this resonance, has a large effect on the manner in which vibration is transmitted through seats.

Accordingly, it is an aspect of the present disclosure to use mechanical impedance methods to predict and make efforts to maximize the transmissibility of the mechanical vibration energy through a patient standing on an oscillating platform apparatus and performing exercises and/or being treated using dynamic motion therapy for bone fractures, osteopenia, osteoporosis, or other tissue conditions, postural instability, or other conditions, such as cystic fibrosis, Crohn's disease and kidney and gall bladder stones, as described in U.S. patent application Ser. No. 11/207,335 filed on Aug. 18, 2005; the entire contents of the provisional patent application are incorporated herein by reference.

It is also an aspect of the present disclosure to use mechanical impedance methods in designing a seat or other support structure to be supported by the oscillating platform apparatus which will maximize the transmissibility of the mechanical vibration energy through the oscillating platform apparatus-seat/support structure-patient interface.

SUMMARY

The embodiments described herein satisfy the aspects described above. More particularly, apparatus and methods according to various embodiments of the disclosure are disclosed which automatically measure the weight of the patient and adjust dynamic motion treatment characteristics such as, for example, the frequency of oscillation and/or the amplitude of the frequency of oscillation of an oscillating platform apparatus of a dynamic motion therapy system.

The apparatus and methods according to various embodiment of the disclosure further use mechanical impedance methods to predict and make efforts to maximize the transmissibility of the mechanical vibration energy through a patient standing on the oscillating platform apparatus and performing exercises and/or being treated using dynamic motion therapy for bone fractures, osteopenia, osteoporosis, or other tissue conditions, postural instability, or other conditions, such as cystic fibrosis, Crohn's disease and kidney and gall bladder stones, as described in U.S. patent application Ser. No. 11/207,335 filed on Aug. 18, 2005.

The disclosure further discloses using mechanical impedance methods in the design of a seat or other support structure to be supported by the oscillating platform apparatus and used by a patient during dynamic motion therapy for maximizing the transmissibility of the mechanical vibration energy through the oscillating platform apparatus-seat/support structure-patient interface. An oscillating platform apparatus according to the invention is also referred to as an "oscillating platform" or as a "mechanical stress platform."

One aspect of apparatus and methods according to various embodiments of the disclosure focuses on a platform for therapeutically treating bone fractures, osteopenia, osteoporosis, or other tissue conditions, postural instability, or other conditions, such as cystic fibrosis, Crohn's disease and kidney and gall bladder stones, having the ability to automatically measure the weight of the body being supported by the platform. An oscillating actuator is positioned within the oscillating platform apparatus and is configured to impart an oscillating force on the body.

Circuitry associated with the oscillating platform apparatus automatically determines the weight of the body being supported on the oscillating platform apparatus. Once the weight of the body is determined, at least one operating parameter (the amplitude of a frequency of the oscillating force and/or frequency of the oscillating force) of the oscillating actuator is adjusted using at least one feedback signal (closed loop control) to provide a desired therapeutic treatment to the patient.

The associated circuitry includes two accelerometers mounted to the oscillating platform apparatus and a digital signal processor for receiving information from the two accelerometers and for transmitting control signals to the oscillating actuator to control the operating parameters of the oscillating actuator accordingly. One accelerometer is mounted to an upper or vibrating plate of the oscillating platform apparatus and the other accelerometer is mounted to a drive or vibrating lever within the oscillating platform apparatus.

The accelerometer mounted to the upper plate transmits patient acceleration information during dynamic motion therapy to the digital signal processor for use in determining the acceleration of the patient either standing on the platform or being supported by a support structure resting on the platform in real time. The digital signal processor transmits a feedback signal whose amplitude is adjusted to the oscillating actuator. The feedback signal is used to maintain a predetermined number used for automatic gain control (closed loop control) within a predetermined range having predetermined upper and lower limits. The digital signal processor adds the predetermined number and the acceleration of the patient continuously or periodically during dynamic motion therapy to determine the average acceleration of the patient over time.

The average acceleration is stored within a memory of the processor to be used for patient monitoring and other purposes.

The accelerometer mounted to the drive lever transmits tilt information to the digital signal processor and accordingly functions as a patient sensing device (determines presence of patient), weight monitoring sensor, transmissibility (dynamic stiffness) coefficient sensor, and patient compliance monitor. This accelerometer transmits a first angular measurement to the digital signal processor after power-on and before the patient stands on the upper plate (or is supported by a support structure resting on the platform). This angular measurement is used to determine the initial angle of the upper plate which is dependent on the actual horizontality of the installation surface upon which the oscillating platform apparatus rests. Another angular measurement is received by the digital signal processor from this accelerometer after the patient stands on the upper plate (or is supported by the support structure resting on the platform) and before the oscillating actuator is actuated. This angular measurement is used together with the other angular measurement for calibrating the oscillating platform apparatus and for calculating the weight of the patient using conventional weight/angle equations. The weight is preferably stored in a memory of the digital processor.

It is contemplated that if the digital signal processor has not received patient acceleration information or angular measurements after a predetermined time period from the respective accelerometers, the digital signal processor turns off the oscillating actuator. This conserves power when a patient is not standing on the oscillating platform apparatus or being supported by the support structure, such as a seat or exercise equipment, resting on the oscillating platform apparatus.

During dynamic motion therapy, the digital signal processor determines and monitors the weight of the patient. The weight of the patient is continuously in real time or periodically compared to the original stored weight to determine the posture of the patient and accordingly, the transmissibility of the mechanical vibration energy through the patient or oscillating platform apparatus-seat/support structure-patient interface, since the posture of the patient and dynamic stiffness of the seat/support structure affects the transmissibility of the mechanical vibration energy through the patient.

If the calculated weight during dynamic motion therapy differs significantly (i.e., more than a predetermined threshold) from the original stored weight, the digital signal processor determines that the patient's posture changed thereby decreasing or increasing the transmissibility of the mechanical vibration energy depending on whether the weight decreased (transmissibility decreased) or increased (transmissibility increased). If the weight decreased, it can be assumed that the patient has deviated from or is not compliant with the dynamic motion therapy treatment protocol. Accordingly, by adjusting the posture and/or dynamic stiffness of the seat (or other support structure) resting on the oscillating platform apparatus to bring the calculated weight to approximate the original stored weight, the transmissibility of the mechanical vibration energy through the patient or oscillating platform apparatus-seat/support structure-patient interface can be influenced, as well as dynamic loading, for maximizing the treatment effects caused by dynamic motion therapy.

Objects, features and advantages of various apparatus and methods according to various embodiments of the disclosure include but not limited to:

(1) providing the ability to automatically determine the weight of a body and adjust the amplitude of the frequency of the oscillating force and/or frequency of the oscillating force used to therapeutically treat damaged tissues, bone fractures, osteopenia, osteoporosis, or other tissue conditions, postural instability, or other conditions, such as cystic fibrosis, Crohn's disease and kidney and gall bladder stones;

(2) providing the ability to therapeutically treat tissues in a body to reduce or prevent osteopenia or osteoporosis;

(3) providing the ability to therapeutically treat damaged tissues, bone fractures, osteopenia, osteoporosis, or other tissue conditions in a body at a frequency effective to promote tissue or bone healing, growth, and/or regeneration;

(4) providing an apparatus adapted to automatically therapeutically treat damaged tissues, bone fractures, osteopenia, osteoporosis, or other tissue conditions in a body;

(5) providing the ability to turn an oscillating actuator on and off based on the existence of a body on an oscillator platform apparatus;

(6) providing the ability to continuously or periodically monitor a patient's posture and accordingly influence the transmissibility of the mechanical vibration energy through the patient's body;

(7) providing the ability to use mechanical impedance methods to predict the transmissibility of a seat using the dynamic stiffness of the seat and the apparent weight of the body;

(8) providing the ability to measure the acceleration of a patient undergoing dynamic motion therapy without placing sensors or other objects on the patient's body; and (9) providing the ability to custom design a support structure, such as a seat, exercise device, etc., having maximum transmissibility of the mechanical vibration energy through the oscillating platform apparatus-support structure-patient interface.

DETAILED DESCRIPTION OF PREFERRED EMBODIMENTS

Apparatus and methods in accordance with various embodiments of the disclosure are for therapeutically treating tissue damage, bone fractures, osteopenia, osteoporosis, or other tissue conditions, postural instability, or other conditions, such as cystic fibrosis, Crohn's disease and kidney and gall bladder stones. Furthermore, apparatus and methods in accordance with various embodiments of the disclosure provide a dynamic motion therapy system having an oscillating platform apparatus that is highly stable, and relatively insensitive to positioning of the patient on the platform, while providing low displacement, high frequency mechanical loading of bone tissue sufficient to promote healing and/or growth of tissue damage, bone tissue, or reduce, reverse, or prevent osteopenia and osteoporosis, and other tissue conditions, postural instability, or other conditions, such as cystic fibrosis, Crohn's disease and kidney and gall bladder stones.

Figure 1:
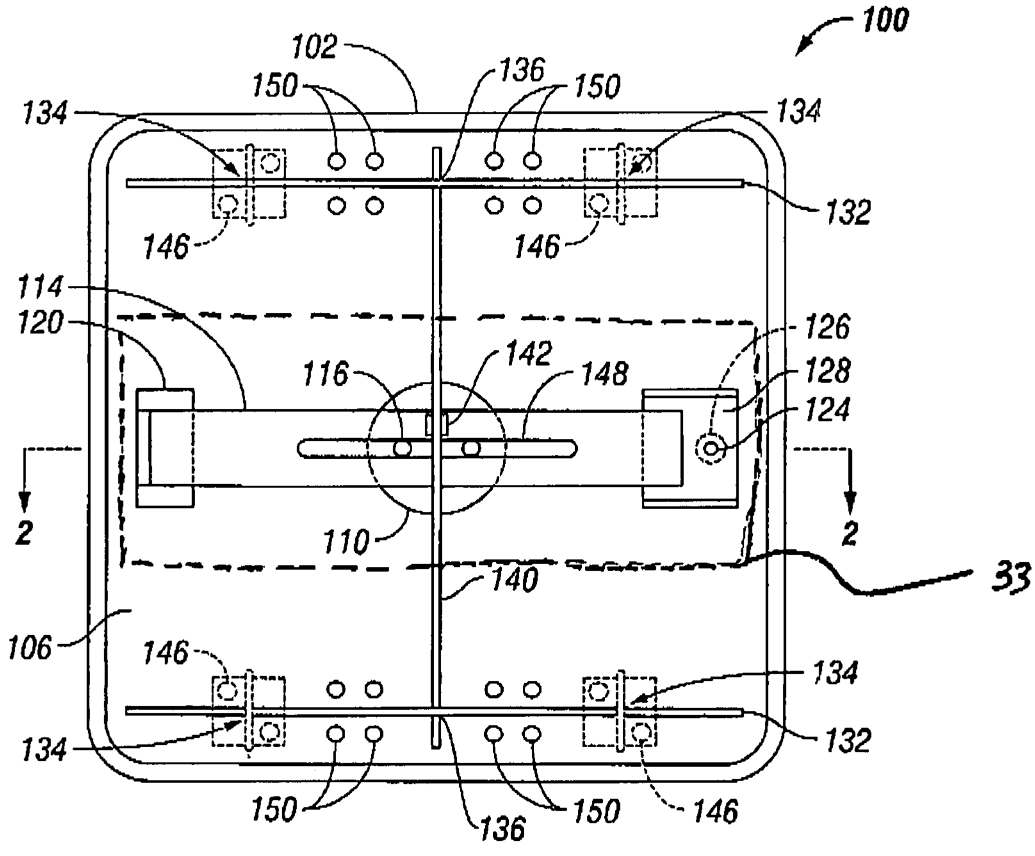
FIG. 1 is a top plan view of an oscillating platform apparatus of a dynamic motion therapy system according to the disclosure, viewed through the top plate, and showing the internal mechanism of the oscillating platform apparatus.

FIGS. 1-4 illustrate an oscillating platform according to an embodiment of the disclosure. FIG. 1 shows a top plan view of the platform 100, which is housed within a housing 102. The oscillating platform apparatus 100 is also referred to as an oscillating platform, platform, vibration table or a mechanical stress platform. The housing 102 includes an upper plate 104 (best seen in FIGS. 2 and 3), lower plate 106, and side walls 108. Note that the upper plate 104 is generally rectangular or square-shaped, but can otherwise be geometrically configured for supporting a body in an upright position on top of the upper plate 104, or in a position otherwise relative to the platform 100. Other configurations or structures can be also used to support a body in an upright position, above, or otherwise relative to, the platform.

FIG. 1 shows the platform 100 through top plate 104, so that the internal mechanism or oscillating mechanism 33 can be illustrated. An oscillating actuator 110 mounts to lower plate 106 by oscillator mounting plate 112 (see FIG. 2), and connects to drive lever 114 of oscillating mechanism 33 by one or more connectors 116.

Oscillating actuator 110 causes drive lever 114 to rotate a fixed distance around drive lever pivot point 118 on drive lever mounting block 120 of oscillating mechanism 33. The oscillating actuator 110 actuates the drive lever 114 at a first predetermined frequency. The motion of the drive lever 114 around the drive lever pivot point 118 is damped by a damping member of oscillating mechanism 33 such as a spring 122, best seen in FIGS. 2 and 3. The damping member or spring 122 creates an oscillation force to counteract the weight on platform and the voice coil 126. The oscillation force of the spring 122 operates at a second predetermined frequency. The second predetermined frequency is preferably equal to the first predetermined frequency. One end of spring 122 is connected to spring mounting post 124, which is supported by mounting block 126, while the other end of spring 122 is connected to distributing lever support platform 128. Distributing lever support platform 128 is connected to drive lever 114 by connecting plate 130 (FIG. 3). Driver lever 114 supports primary distributing lever 140, which rotates about primary distributing lever pivot point 142. Secondary distributing levers 132 are connected to primary distributing lever 140 by linkages 136, which may be simply mutually engaging slots. Secondary distributing levers 132 rotate about pivot points 134 in a manner similar to that described above for the primary distributing lever 140 and are supported by supports 138 extending from lower plate 106.

Upper plate 104 is supported by a plurality of contact points 146, which can be adjustably secured to the underside of the upper plate 104, and which contact components of the oscillating mechanism 33, i.e., the upper surface of primary distributing lever 140, upper surfaces of secondary distributing levers 132, or a combination thereof.

In operation, a patient (not shown) sits or stands on the upper plate 104 (or is supported by a support structure resting on the platform 100), which is in turn supported by a primary distributing lever 140, secondary distributing levers 132, or a combination thereof. When the platform 100 of the dynamic motion therapy system 400 is operating, oscillating actuator 110 moves up and down in a reciprocal motion, causing drive lever 114 of oscillating mechanism 33 to oscillate about its pivot point 118 at a first predetermined frequency. The rigid connection between the drive lever 114 and distributing lever support platform 128 results in this oscillation being damped by the force created or exerted by the spring 122, which can desirably be driven at a second predetermined frequency, in some embodiments its resonance frequency and/or harmonic or sub-harmonics of the resonance frequency. The oscillatory displacement is transmitted from the distributing lever support platform 128 to primary distributing lever 140 and thus to secondary distributing levers 132. One or more of the primary distributing lever 140 and/or secondary distributing levers 132 distribute the motion imparted by the oscillation to the free-floating upper plate 104. The oscillatory displacement is then transmitted to the patient supported by the upper plate 104, thereby imparting high frequency, low displacement mechanical loads to the patient's tissues, such as the bone structure of the patient supported by the platform 100.

In this particular embodiment, the oscillating actuator 110 can be a piezoelectric or electromagnetic transducer configured to generate a vibration. Other conventional types of transducers may be suitable for use with the invention. For example, if small ranges of displacements are contemplated, e.g. approximately 0.002 inches (0.05 mm) or less, then a piezoelectric transducer, a motor with a cam, or a hydraulic-driven cylinder can be employed. Alternatively, if relatively larger ranges of displacements are contemplated, then an electromagnetic transducer can be employed.

Suitable electromagnetic transducers, such as a cylindrically configured moving coil high performance linear actuator may be obtained from BEI Motion Systems Company, Kimco Magnetic Division of San Marcos, Calif. Such an electromagnetic transducer may deliver a linear force, without hysteresis, for coil excitation in the range of 10-100 Hz, and short-stroke action in ranges as low as 0.8 inches (20 mm) or less.

Furthermore, the spring 122 can be a conventional type spring configured to resonate at a predetermined frequency as a function of the mass of the patient, or at the resonance frequency. The resonance frequency of the spring can be determined from the equation:

$$\text{Resonance Frequency (Hz)}=(\tfrac{1}{2}*3.14)*[\text{Spring Constant (k)/Mass (lbs)}]^{1/2}$$

For example, if the oscillating platform apparatus is to be designed for treatment of humans, the spring 122 can be sized to resonate at a frequency between approximately 30-36 Hz. If the oscillating platform apparatus is to be designed for the treatment of animals, the spring 122 can be sized to resonate at a frequency up to 120 Hz. An oscillating platform apparatus configured to oscillate at approximately 30-36 Hz utilizes a compression spring with a spring constant (k) of approximately 9 pounds (lbs.) per inch in the embodiment shown. In other configurations of an oscillating platform apparatus, oscillations of a similar range and frequency can be generated by one or more springs, or by other devices or mechanisms designed to create or otherwise dampen an oscillation force to a desired range or frequency.

Figure 2:
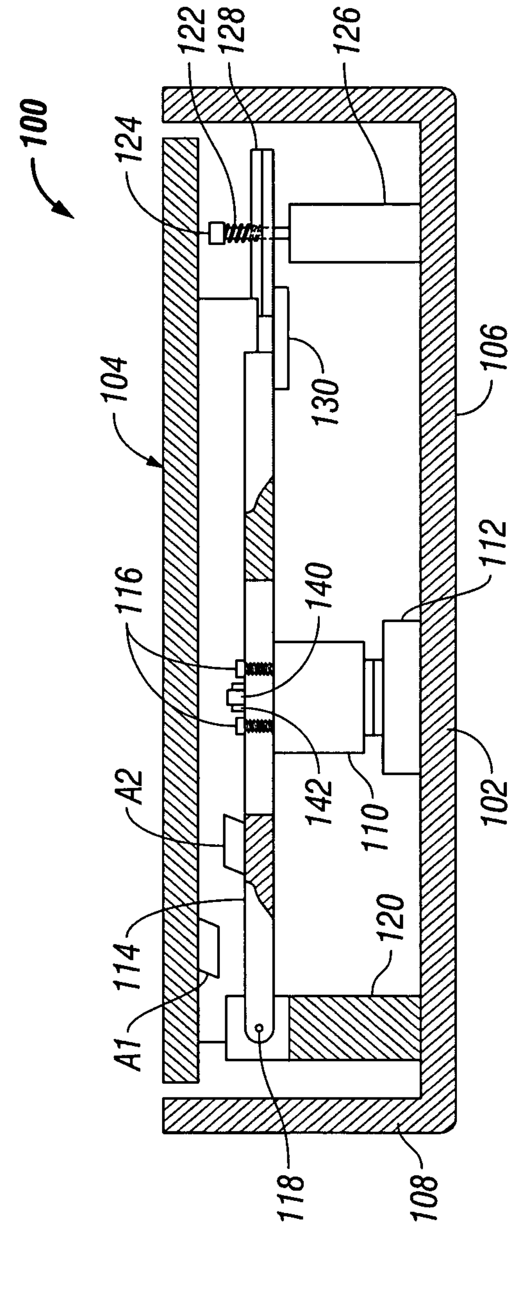
FIG. 2 is a side sectional view taken along line 2-2 in FIG. 1, and partially cut away to show details of the connection of the oscillating actuator to the drive lever and the arrangement of the two accelerometers.
Figure 3:
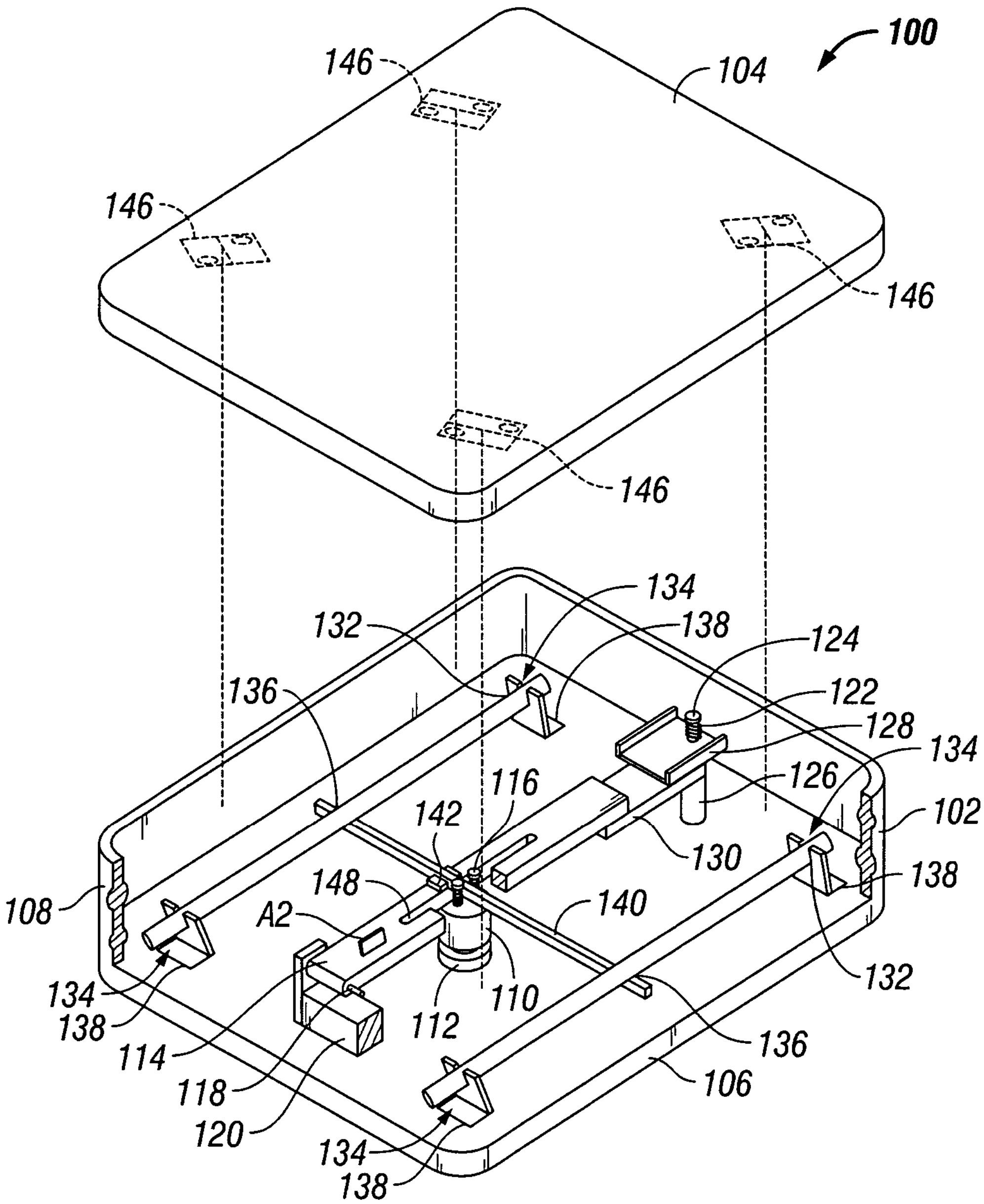
FIG. 3 is an exploded perspective view of the oscillating platform apparatus shown in FIG. 1, and partially cut away to show the internal mechanism of the oscillating platform apparatus.

FIG. 2 is a side sectional view taken along line 1—1 in FIG. 1, and partially cut away to show details of the connection of the oscillating actuator 110 to the drive lever 114. The drive lever 114 includes an elongate slot 148 (shown in FIGS. 1 and 3) for receiving connectors 116. The elongate slot 148 permits the oscillating actuator 110 to be selectively positioned along a portion of the length of the drive lever 114. The connectors 116 can be manually adjusted to position the oscillating actuator 110 with respect to the drive lever 114, and then readjusted when a desired position for the oscillating actuator 110 is selected along the length of the elongate slot 148. By adjusting the position of the oscillating actuator 110, the vertical movement or displacement of the drive lever 114 can be adjusted. For example, if the oscillating actuator 110 is positioned towards the drive lever pivot point 118, then the vertical movement or displacement of the drive lever 114 at the opposing end near the spring 122 will be relatively greater than when the oscillating actuator 110 is positioned towards the spring. Conversely, as the oscillating actuator 110 is positioned towards the spring 122, the vertical movement or displacement of the drive lever 114 at the opposing end near the spring 122 will be relatively less than when the oscillating actuator 110 is positioned towards the drive lever pivot point 118.

FIG. 3 is an exploded perspective view of the oscillating platform 100 shown in FIG. 1, and is partially cut away to show the internal mechanism of the platform 100. In this embodiment as well as other embodiments, the oscillating platform 100 is contained within a housing 102. The housing 102 can be made from any material sufficiently strong for the purposes described herein, e.g. any material that can bear the weight of a patient on the upper plate. For example, suitable materials can be metals, e.g. steel, aluminum, iron, etc.; plastics, e.g. polycarbonates, polyvinylchloride, acrylics, polyolefins, etc.; or composites; or combinations of any of these materials.

Also shown in this embodiment is a series of holes 150 machined through the upper plate 104 of the platform 100. The holes 150 are arranged parallel with each of the primary distributing lever 140 and secondary distributing levers 132. These holes 150 (also shown in FIG. 1) provide different points of connection or attachment for contact points 146, thereby varying the points at which these contact points contact the distributing levers 132, 140, and thus the amount of lever arm and mechanical advantage used in driving the upper plate 104 to vibrate.

Figure 4:
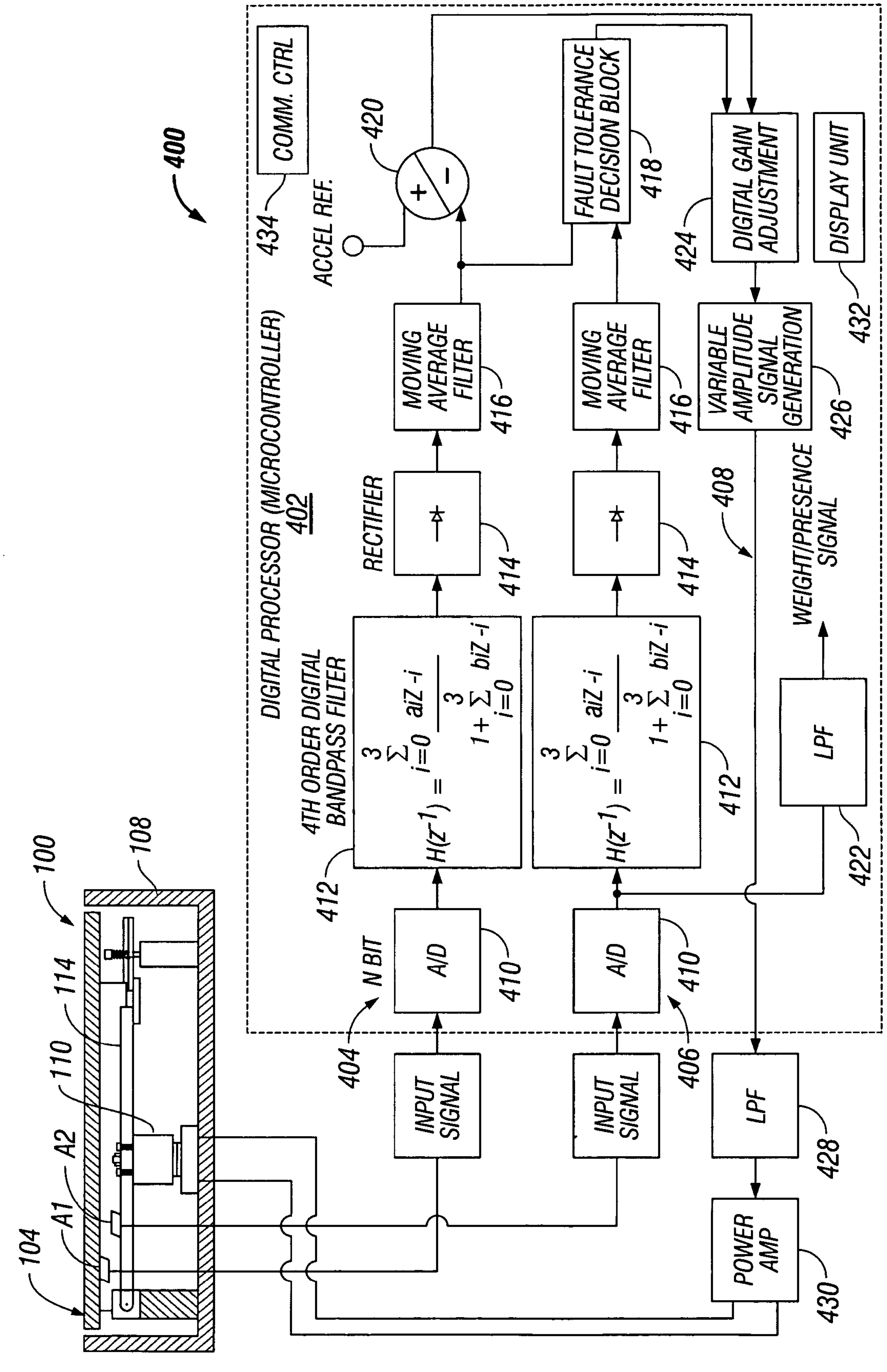
FIG. 4 is schematic block diagram of the dynamic motion therapy system in accordance with the present disclosure and showing the oscillating platform apparatus shown by FIG. 1.

As shown in FIG. 2, an accelerometer A1 is positioned on an underside surface of the upper plate 104 for transmitting at least one signal relaying patient acceleration information to a digital signal processor 402 as shown in FIG. 4. The acceleration information is processed by the processor 402 for determining the acceleration of the patient either standing on the upper plate 104 or being supported by a support structure resting on the platform 100 in real time. The processor 402 can be housed within the platform 100.

The processor 402 transmits a feedback signal to an oscillating actuator 110. The feedback signal is preferably a sine wave whose amplitude is adjusted for maintaining a predetermined number used for automatic gain control (closed loop control) within a predetermined range having predetermined upper and lower limits. The digital signal processor 402 adds the predetermined number and the acceleration of the patient continuously or periodically during dynamic motion therapy to determine the average acceleration of the patient over time. The average acceleration is stored within a memory of the processor 402 to be used for patient monitoring and other purposes. A second accelerometer A2 is mounted to the drive lever 114 and transmits at least one signal relaying tilt information to the digital signal processor 402 as shown in FIG. 4, such as by measuring the angular displacement of drive lever 114. Accelerometer A2 performs the functions of a patient sensing device (determines presence of patient), weight monitoring sensor, transmissibility (dynamic stiffness) coefficient sensor, and patient compliance monitor. Accelerometer A2 transmits a first angular measurement to the digital signal processor 402 after power-on and before the patient stands on the upper plate 104 (or is supported by a support structure resting on the platform 100). This angular measurement is used to determine the initial angle of the upper plate 104 which is dependent on the actual horizontality of the installation surface upon which the oscillating platform apparatus 100 rests. Another angular measurement is received by the digital signal processor 402 from accelerometer A2 after the patient stands on the upper plate 104 (or is supported by the support structure resting on the platform 100) and before the oscillating actuator 110 is actuated. This angular measurement is used together with the other angular measurement for calibrating the oscillating platform apparatus 100 and for calculating the weight of the patient using conventional weight/angle equations. The weight is preferably stored in a memory of the digital processor 402.

It is contemplated that if the digital signal processor 402 has not received patient acceleration information or angular measurements after a predetermined time period from the respective accelerometers A1, A2, the digital signal processor 402 turns off the oscillating actuator 110. This conserves power when a patient is not standing on the oscillating platform apparatus 100 or being supported by the support structure, such as a seat or exercise equipment, resting on the oscillating platform apparatus 100.

During dynamic motion therapy, the digital signal processor 402 determines and monitors the weight of the patient. The weight of the patient is continuously measured in real time or periodically compared to the original stored weight to determine the posture of the patient and accordingly, the transmissibility of the mechanical vibration energy through the patient or oscillating platform apparatus-seat/support structure-patient interface, since the posture of the patient and dynamic stiffness of the seat/support structure affects the transmissibility of the mechanical vibration energy through the patient.

If the calculated weight during dynamic motion therapy differs significantly (i.e., more than a predetermined threshold) from the original stored weight, the digital signal processor 402 determines that the patient's posture changed thereby decreasing or increasing the transmissibility of the mechanical vibration energy depending on whether the weight decreased (transmissibility decreased) or increased (transmissibility increased). If the weight decreased, it can be assumed that the patient has deviated from or is not compliant with the dynamic motion therapy treatment protocol. Accordingly, by adjusting the posture of the patient and/or dynamic stiffness of the seat (or other support structure) resting on the oscillating platform apparatus 100, the calculated weight can be made to approximate the original stored weight, and thus, the transmissibility of the mechanical vibration energy through the patient or oscillating platform apparatus-seat/support structure-patient interface can be influenced, as well as dynamic loading, for maximizing the treatment effects caused by dynamic motion therapy.

With reference to FIG. 4, there is shown a schematic block diagram of the dynamic motion therapy system 400 in accordance with the disclosure. The dynamic motion therapy system 400 includes platform 100 having two accelerometers A1, A2 for transmitting information to the digital signal processor 402. The digital signal processor 402 includes primarily two incoming data paths 404, 406 having identical components for processing data received from the two accelerometers A1, A2 and one outgoing data path 408 for relaying control or feedback signals to the oscillating actuator 110.

The digital signal processor 402 includes a memory storing a set of programmable instructions capable of being executed by the digital signal processor 402 for operating the components of the two incoming data paths 404, 406 and one outgoing data path 408 for performing the functions described above in accordance with the disclosure, as well as other functions. The set of programmable instructions can also be stored on a computer-readable medium, such as a CD-ROM, diskette, and other magnetic media, and downloaded to the digital signal processor 402.

Each incoming data path includes four major components for processing the incoming data from the two accelerometers A1, A2. The four major components are in order from left to right in FIG. 4 an analog-to-digital (A/D) converter 410, a bandpass filter 412, a rectifier 414, a moving average filter 416, and a fault tolerance decision block 418.

Preferably, the bandpass filter 412 in each incoming data path is a $4^{th}$ order elliptic bandpass filter which finds the "sweet spot" for each particular patient (this causes the processor to shift the resonance of the dynamic therapy system 400 based on the patient's weight by transmitting a signal to the oscillating actuator 110 to change the frequency of the oscillating force). The digital signal processor 402 processes the polynomial coefficients of the $4^{th}$ order elliptic bandpass filters by implementing "power of two" coefficients. The processor 402 is programmed to do this instead of performing polynomial multiplication for each coefficient in the polynomial which would require a significantly longer processing time. The processor 402 in accordance with the present disclosure reduces processing time by implementing the polynomial coefficients using the "power of two." For example, if the coefficient is 3.93215, the processor 402 can perform a quick approximation of the coefficient by approximating the coefficient as follows: $4-1/16+3/128-1/512$. It is contemplated that the same method can be used to process the coefficients of the other filters of the processor 402.

The output from the moving average filter 416 of incoming data path 404 is provided to the fault tolerance decision block 418 for determining fault tolerance level and an adder/subtracter block 420 for deciding whether to increase or decrease the gain to maintain the average vibration intensity to a preset value. The output of block 420 is an error signal which determines whether to increase or decrease the vibration level of the oscillating actuator 110.

The output from the adder/subtractor block 420 is the acceleration of the patient and the output from A/D converter 410 of incoming data path 406 is provided to a low-pass filter 422 which outputs a weight/presence signal. The weight/presence signal is used to sense the presence of the patient and to calculate the weight of the patient continuously or periodically using conventional weight/angle equations during dynamic motion therapy.

By determining the weight of the patient during treatment and comparing the weight to the original stored weight as described above, the processor 402 is able to determine whether the patient is compliant with the treatment protocols (e.g., proper stance or position) and the posture of the patient for determining the transmissibility of the mechanical vibration energy through the patient. The patient can then influence the transmissibility, if necessary (i.e., if the calculated weight indicates poor transmissibility), by shifting or changing his posture accordingly.

The acceleration value of the patient and the output from the fault tolerance decision block 418 are inputs at separate times (since the processor 402 of the dynamic motion therapy system 400 is designed as a real time interrupt driven software system as described below) during operation of the dynamic therapy system 400 to the outgoing data path 408.

The outgoing data path 408 includes four major components for processing control and feedback signals transmitted from the processor 402 to the oscillating actuator 110. The four major components are in order from right to left in FIG. 4 a digital gain adjustment module 424 for performing automatic gain control as described above, a variable amplitude signal generation module 426 for increasing or decreasing the sinusoidal signal driving the oscillating actuator 110, a low-pass filter 428 for filtering the control and feedback signals and a power amplifier 430 for amplifying the control and feedback signals.

Accordingly, as shown in FIG. 4, the output from Al is filtered by a first bandpass filter 412, the output of which is a first signal provided to the fault tolerance decision block 418. The output from A2 is filtered by a second bandpass filter 412, the output of which is a second signal which also provided to the fault tolerance decision block 418. The output from the fault tolerance decision block 418 is further processed and output as a control signal for controlling at least one parameter of the oscillating actuator 110. The output from A2 follows a separate data path than the one in which the A2 output signal is filtered by bandpass filter 412. Here, the output from A2 is filtered by low-pass filter 422, the output of which is a third signal, the weight/presence signal, which is used for determining at least one of whether a body is present on the platform, and the weight of the body supported on the platform.

The system 400 includes a display unit 432 for displaying treatment-related information and other information, such as diagnostic information, to the patient, medical professional or other individual. The treatment-related information can include the original calculated weight of the patient and the calculated weight of the patient during treatment, the acceleration of the patient, automatic gain control information, level or degree of compliance to the treatment protocols, a transmissibility value indicating or approximating the transmissibility of the mechanical vibration energy, etc.

The digital signal processor 402 of the dynamic motion therapy system 400 is designed as a real time interrupt driven software system (the system 400 does not have a main loop). A timer interrupt occurs every 1/fs milliseconds. That is, for example, if the system 400 is tuned at 34 Hz, a timer interrupt occurs every 1/34 seconds. A different function occurs during each timer interrupt, such as replenishing or updating the display unit 432, transmitting the control or feedback signals to the oscillating actuator 110, and generating a transmitting a sine wave to the oscillating actuator 110 for automatic gain control (the sine wave is preferably generated and transmitted approximately 500 times per second). It is contemplated that higher priority interrupts are performed first. If there is not interrupt to be performed, the processor 402 goes into an idle mode until there is an interrupt to perform.

The digital signal processor 402 generates the (sinusoidal) signal to the oscillating actuator 110 and processes the acceleration signal received from accelerometer A1 using at least one digital bandpass filter 412 with a variable sampling rate during calibration (tuning) of the dynamic motion therapy system 400. In the dynamic motion therapy system 400, the sampling rate and thus the vibration frequency is between 0 and 250 Hz, with the at least one digital bandpass filter 412 adaptively tuned to the current operating frequency. The variable sampling rate is possible due to the interrupt driven software system of the software control loop as described above.

The dynamic therapy system 400 further includes communication circuitry 434 for downloading/uploading data, including software updates, to the processor 402 and for communicating with a remote processor of a central monitoring station via at least one network, such as the Internet, including receiving Internet content. The communication circuitry 434 can include RS232, USB, parallel and serial ports and associated circuitry, as well as network connection software and circuitry, such as a modem, DSL connection circuitry, etc. Preferably, the process of downloading/uploading data, including software updates, is configured as an interrupt for being performed during a timer interrupt by the dynamic therapy system 400.

Patient compliant data (directed to whether the patient is compliant to at least one treatment protocol or regiment) and other patient- and treatment-related data are preferably stored in the dynamic therapy system 400 for evaluation at a later time or for transmission via the network using the communications circuitry 434 to the central monitoring station for observation. The transmission can also occur in real time during dynamic motion therapy for enabling a medical professional or other observer to transmit data via the network to the patient during the therapy session. The transmitted data can be displayed to the patient on the display unit 432 and/or audibly played via a speaker.

The transmitted data can include a message for the patient to change his posture for maximizing mechanical impedance and the transmissibility of the mechanical vibration energy through the patient. Another transmitted message can be for the patient to manually change one or more operating parameters of the dynamic therapy system 400.

The data transmitted from the dynamic therapy system 400 can include video and/or sensor data obtained by a video camera and/or at least one sensor mounted to the support structure or the dynamic therapy system 400 and transmitted via the network to the central monitoring station.

Using the dynamic therapy system 400 and mechanical impedance methods as known in the art, one can predict the transmissibility of the mechanical vibration energy through the patient being supported by a support structure, such as a kneeling chair-type support structure, wheel chair, seat, exercise device, etc., using the dynamic stiffness of the support structure and the apparent weight of the body measured at appropriate vibration magnitudes. The materials, structure, orientation, etc. of the support structure can then be selected and re-designed for maximizing the transmissibility of the mechanical vibration energy through the oscillating platform apparatus-support structure-patient interface in order to maximize the transmissibility of the mechanical vibration energy through the patient. The support structure can in effect be custom designed for each patient for maximizing the transmissibility of the mechanical vibration energy through the patient.

It is understood that changes may be made in the particular embodiments disclosed herein which are within the scope and spirit of the disclosure as outlined by the appended claims. Having thus described the disclosed embodiments with the details and particularity required by the patent laws, what is claimed and desired protected by Letters Patent is set forth in the appended claims.

What is claimed is:

1. An apparatus for therapeutically treating a tissue in a body, the apparatus comprising:

a platform configured to support the body;

a lever assembly operatively coupled to the platform;

an oscillator operatively coupled to the platform, the oscillator further applying an oscillating force to the lever assembly thus causing the platform to oscillate for imparting varying mechanical vibration energy on the body for therapeutically treating a tissue in the body;

an accelerometer operatively coupled to the platform for measuring an angular displacement indicative of tilt of the platform and transmitting a corresponding signal indicative of the weight of the body supported on the platform; and a processor for processing output from the accelerometer for using the output from the accelerometer for determining the weight of the body.

2. The apparatus of claim 1, wherein the platform comprises:

an upper plate and a lower plate;

and wherein the lever assembly further comprises:

a drive lever supported from the lower plate, wherein the mechanical vibration energy is imparted on the body by oscillating the drive lever with respect to the upper plate and lower plate at the predetermined frequency; and a damping member configured to create an oscillation force at another predetermined frequency;

wherein the distributing lever arm is configured to receive the mechanical vibration energy from the damping member and to transfer a portion of the mechanical vibration energy to the upper plate via the pair of substantially parallel levers.

3. The apparatus of claim 1, wherein the apparatus is an interrupt driven apparatus.

4. The apparatus of claim 1, wherein the angular displacement is the angular displacement of a lever of the lever assembly.

5. The apparatus of claim 1, wherein the lever assembly comprises a drive lever operatively coupled to a distributing lever, and a pair of substantially parallel levers supported by the distributing lever arm arranged substantially perpendicular with respect to each of the pair of substantially parallel levers, wherein the drive lever is actuated by the oscillator.

6. The apparatus of claim 1, wherein the processor comprises:

a bandpass filter for filtering output from the accelerometer to form a first signal component; and a low-pass filter for filtering output from the accelerometer to form a second signal component, wherein the second signal component has a different characteristic than the first signal component.

7. The apparatus of claim 6, wherein the apparatus further comprises:

a second accelerometer operatively coupled to the platform for measuring acceleration of the body;

wherein the processor processes output from the second accelerometer and outputs a control signal for controlling the oscillator for adjusting at least one parameter of the oscillation force.

8. The apparatus of claim 7, wherein the processor further comprises a first and second bandpass filter for filtering output from the first and second accelerometers, respectively, wherein the first and second bandpass filters are each programmed to process polynomial coefficients by approximating the polynomial coefficients by power of two coefficients.

9. The apparatus of claim 7, wherein the processor further comprises:

a third filter for filtering output from the second accelerometer; and a fault tolerance decision block receiving output from the third filter and the first signal component, wherein output from the fault tolerance decision block is used for generating the control signal.

10. The apparatus of claim 1, wherein the processor comprises:

a low-pass filter for filtering output from the accelerometer and outputting a corresponding weight/presence signal which is used for determining at least one of whether a body is present on the platform, and the weight of the body supported on the platform.

11. The apparatus of claim 10, wherein the oscillator is configured such that the oscillating force is set to zero when the weight presence signal indicates that the body is not present on the platform.

12. The apparatus of claim 10, wherein the oscillator is further configured such that the oscillating force is set to a desired level when the weight presence signal indicates that the weight of the body being supported on the platform changes from zero to a magnitude which is greater than zero.

13. The apparatus of claim 10, wherein the output from the low-pass filter is further used for determining at least one of whether a posture of the body supported on the platform is compliant with a predetermined treatment plan, and an indication of transmissibility of the vibration energy through the body.

14. A dynamic motion therapy system comprising:
an oscillating platform comprising:
a first plate configured to support a body thereon;
a second plate positioned beneath the first plate;
an oscillating actuator operatively coupled to the second plate; and
an oscillating mechanism in operative communication with the oscillating actuator and the first plate, wherein the oscillating mechanism applies an oscillating force to the oscillating actuator for causing the platform to move in an oscillating fashion for imparting a varying mechanical vibration energy on the body for therapeutically treating a tissue in the body;
a first accelerometer operatively coupled to the first plate and configured to sense movement of the first plate indicative of acceleration of the body supported on the platform;
a second accelerometer operatively coupled to the oscillating mechanism for measuring an angular displacement indicative of tilt of the platform and transmitting a corresponding signal indicative of a weight of the body being supported on the platform; and
a processor for receiving signals from the first and second accelerometers, processing the signal transmitted by the second accelerometer for determining a weight of the body being supported on the platform, and generating and transmitting at least one control signal to the oscillating actuator based on the received signals.

15. The system of claim 14, wherein the at least one control signal adjusts an operating parameter of the oscillating platform.

16. The system of claim 14, wherein the processor includes first and second bandpass filters for filtering output from the first and second accelerometers, respectively, each of the first and second bandpass filters programmed to process polynomial coefficients by approximating the polynomial coefficients by power of two coefficients.

17. The system of claim 14, wherein the oscillating mechanism comprises:
a drive lever supported from the second plate, wherein the mechanical vibration energy is imparted on the body by oscillating the drive lever with respect to the first and second plates the predetermined frequency;
a damping member configured to create an oscillation force at another predetermined frequency; and
a distributing lever arm configured to receive the mechanical vibration energy from the damping member and to transfer a portion of the mechanical vibration energy to the first plate.

18. The system of claim 14, wherein the angular displacement is the angular displacement of a drive lever of the oscillating mechanism.

19. The system of claim 18, wherein the processor comprises a low-pass filter for filtering the output of the second aceelerometer and determines the weight of the body based on the signal output by the low-pass filter, and further determines transmissibility of the mechanical vibration energy by comparing the determined weight to a stored weight corresponding to the body.

20. The system of claim 18, wherein the processor determines the weight of the body based on the signal output by the second accelerometer, and further determines a posture of the body by comparing the determined weight to a stored weight corresponding to the body.

21. The system of claim 14, further comprising communication circuitry for receiving data from and transmitting data to a remote processor via at least one network.

22. The system of claim 21, wherein the data transmitted to the remote processor includes patient compliant data related to the signal output by the second accelerometer indicative of whether a patient is compliant to a treatment protocol.

23. The system of claim 21, wherein the data received from the remote processor includes a message to a patient with respect to a posture of the patient.

24. The system of claim 21, wherein the data received from the remote processor includes a message to a patient with respect to changing at least one operating parameter of the system.

25. A method for therapeutically treating a tissue in a body having a weight, the method comprising the steps of:
supporting the body on a platform;
oscillating the platform to impart varying mechanical vibration energy at a predetermined frequency on the body;
measuring an angular displacement associated with a tilt of the platform and indicative of the weight of the body supported on the platform using a first accelerometer operatively coupled to the platform; and
determining the weight of the body, wherein the weight of the body is determined automatically by a processor receiving at least one signal from the first accelerometer.

26. The method of claim 25, further comprising setting the mechanical vibration energy to zero when the processor determines that the weight on the platform is equal to zero.

27. The method of claim 25, further comprising setting the mechanical vibration energy at a desired level when the processor determines that the weight being supported on the platform changes from zero to a value which is greater than zero.

28. The method of claim 25, wherein the predetermined frequency is between 30 and 36 Hz, and the body is a human body.

29. The method of claim 25, wherein the first accelerometer is positioned on a drive lever of the platform.

30. The method of claim 25, further comprising the steps of:
low-pass filtering the output from the first accelerometer; and
generating and transmitting a first signal representative of the weight of the body.

31. The method of claim 30, further comprising the steps of:
measuring by a second accelerometer acceleration at the platform;
filtering output from the second accelerometer and generating and transmitting a second signal representative of the acceleration of the body supported on the platform;
filtering output from the first accelerometer and generating and transmitting a third signal;

generating a feedback signal by the processor for adjusting the frequency of the oscillating force based on the second and third signals.

32. The method of claim 31, wherein the filtering resulting in the second and third signals is bandpass filtering performed by processing polynomial coefficients by approximating the polynomial coefficients by power of two coefficients.

33. The method of claim 25, further comprising the step of comparing the determined weight of the body to a stored weight of the body for determining the transmissibility of mechanical vibration energy generated by the platform through the body.

34. The method of claim 25, further comprising the step of determining based on the measured angular displacement at least one of whether a body is supported on the platform, whether a posture of the body supported on the platform is compliant with a predetermined treatment plan, and an indication of transmissibility of the vibration energy through the body.

35. A method for therapeutically treating damaged tissues, bone fractures, osteopenia, osteoporosis, postural instability, and organs in a body having a weight, the method comprising the steps of:

supporting the body on a platform;

oscillating the platform to impart varying mechanical vibration energy at a predetermined frequency on the body for therapeutically treating a tissue of the body;

measuring an angular displacement associated with a tilt of the platform and indicative of the weight of the body supported on the platform using an accelerometer operatively coupled to the platform; and determining the weight of the body, wherein the weight of the body is determined automatically by a processor receiving at least one signal from the accelerometer.

36. The method according to claim 35, wherein the determining comprises low-pass filtering the output from the accelerometer.

* * * * *